(12) United States Patent  
Gatzke

(10) Patent No.: US 6,705,992 B2
(45) Date of Patent: Mar. 16, 2004

(54) ULTRASOUND IMAGING ENHANCEMENT TO CLINICAL PATIENT MONITORING FUNCTIONS

(75) Inventor: Ronald D. Gatzke, Lexington, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/086,007

(22) Filed: Feb. 28, 2002

(65) Prior Publication Data

US 2003/0163045 A1 Aug. 28, 2003

(51) Int. Cl.⁷ ................................................ A61B 8/00
(52) U.S. Cl. ...................................................... 600/437
(58) Field of Search ................................. 600/437, 438, 600/440–471, 508; 73/625, 626; 367/7, 11, 130, 138; 128/916; 340/573.1

(56) References Cited

U.S. PATENT DOCUMENTS

| | | | | |
|---|---|---|---|---|
| 4,154,230 A | * | 5/1979 | Lee | 600/440 |
| RE30,397 E | * | 9/1980 | King | 600/437 |
| 5,437,278 A | | 8/1995 | Wilk | |
| 5,722,415 A | * | 3/1998 | Rom et al. | 600/508 |
| 6,438,405 B1 | | 8/2002 | Mooney et al. | |
| 6,497,661 B1 | * | 12/2002 | Brock-Fisher | 600/437 |
| 6,500,118 B1 | * | 12/2002 | Hashimoto | 600/437 |
| 2002/0044059 A1 | * | 4/2002 | Reeder et al. | 340/573.1 |
| 2002/0123688 A1 | * | 9/2002 | Yamauchi | 600/443 |
| 2003/0045796 A1 | * | 3/2003 | Friedman | 600/450 |

* cited by examiner

Primary Examiner—Ali M. Iman
(74) Attorney, Agent, or Firm—John Vodopia

(57) ABSTRACT

An apparatus includes an ultrasound imaging unit integrated into a patient monitoring system continuously generating ultrasound images from a patient and continuously extracting therefrom diagnostic data.

31 Claims, 4 Drawing Sheets

ULTRASOUND IMAGING ENHANCEMENT TO CLINICAL PATIENT MONITORING FUNCTIONS

BACKGROUND OF THE INVENTION

Conventional ultrasound imaging systems used in a clinical setting are presently operated as standalone instruments, typically dedicated to diagnostic image acquisition. In this mode of operation, the ultrasound imaging system is normally used for a short period of time to diagnose a patient. The ultrasound imaging system is also a focused diagnostic system monitoring a particular pathology. An exception to this usage is the use of the transesophageal echocardiogram (TEE) probe in operating room environments for monitoring of cardiac activity during the duration of surgical procedures under active observation by clinical observers. TEE is a test that allows a cardiologist to view images of the internal structures of the heart and the heart's major vessel by inserting an ultrasound probe down the patient's throat or nose. For example, the patient is evaluated for atrial thrombi using the TEE probe.

However, although the TEE test may be four to six hours in duration, the heart is not monitored during the entire duration of the TEE test. Rather, intermittent image snapshots are obtained of the heart and the images are compared, for instance, image snapshots of the heart at pre-surgery are compared to images of the heart at post-surgery. Although, the conventional ultrasound imaging systems may be connected to a hospital's information network, the information network is used primarily for archiving the images and not for doing any diagnostic work or patient management. Further, size and complexity of present ultrasound imaging systems preclude their present use for long term patient monitoring applications.

Modern ultrasound imaging system design is moving towards systems of radically reduced size and complexity. Additionally, increased sophistication of control algorithms in ultrasound imaging systems is rendering the ultrasound imaging systems far more capable of self-adaptation to the imagining environment presented by individual subjects. Further, advancements in the art of information extraction from the ultrasound images allow for improved automatic determination of physiological functionally from the ultrasound image data.

Thus, it is necessary to develop an ultrasound imaging enhancement unit integrated into a patient monitoring system to allow physicians to continuously monitoring physiological functions of a patient from images generated from the ultrasound imaging unit. Rather than limiting the user of the ultrasound imaging unit to diagnostic situations in an emergency room, the ultrasound imaging unit would allow monitoring of non-acute conditions of a patient, such as in intensive-care recovery situations.

SUMMARY OF THE INVENTION

In an exemplary embodiment, the present invention provides for an apparatus, including a patient monitoring system; and an ultrasound imaging unit integrated into the patient monitoring system continuously generating ultrasound images from a patient and continuously extracting therefrom diagnostic data.

The present invention also provides an apparatus including an apparatus, including a patient monitoring system; and a compact standalone ultrasound imaging unit connected to the patient monitoring system continuously collecting ultrasound images from a patient and processing the ultrasound images to continuously extract therefrom diagnostic data.

The present invention is also achieved by a method including: integrating an ultrasound imaging unit to a patient monitoring system; connecting the ultrasound imaging unit to a patient; continuously collecting ultrasound imaging data from the patient; processing the ultrasound imaging data to generate therefrom diagnostic data; continuously transmitting the diagnostic data using a communication channel to a person or to a remote diagnostic system at another location; and analyzing the diagnostic data and determining therefrom a medical treatment for the patient.

These together with other objects and advantages, which will be subsequently apparent, reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

Advantages of the invention will become apparent and more readily appreciated for the following description of the preferred embodiments, taken in conjunction with the accompanying drawings of which.

DETAILED DESCRIPTION OF THE INVENTION

Figure 1:
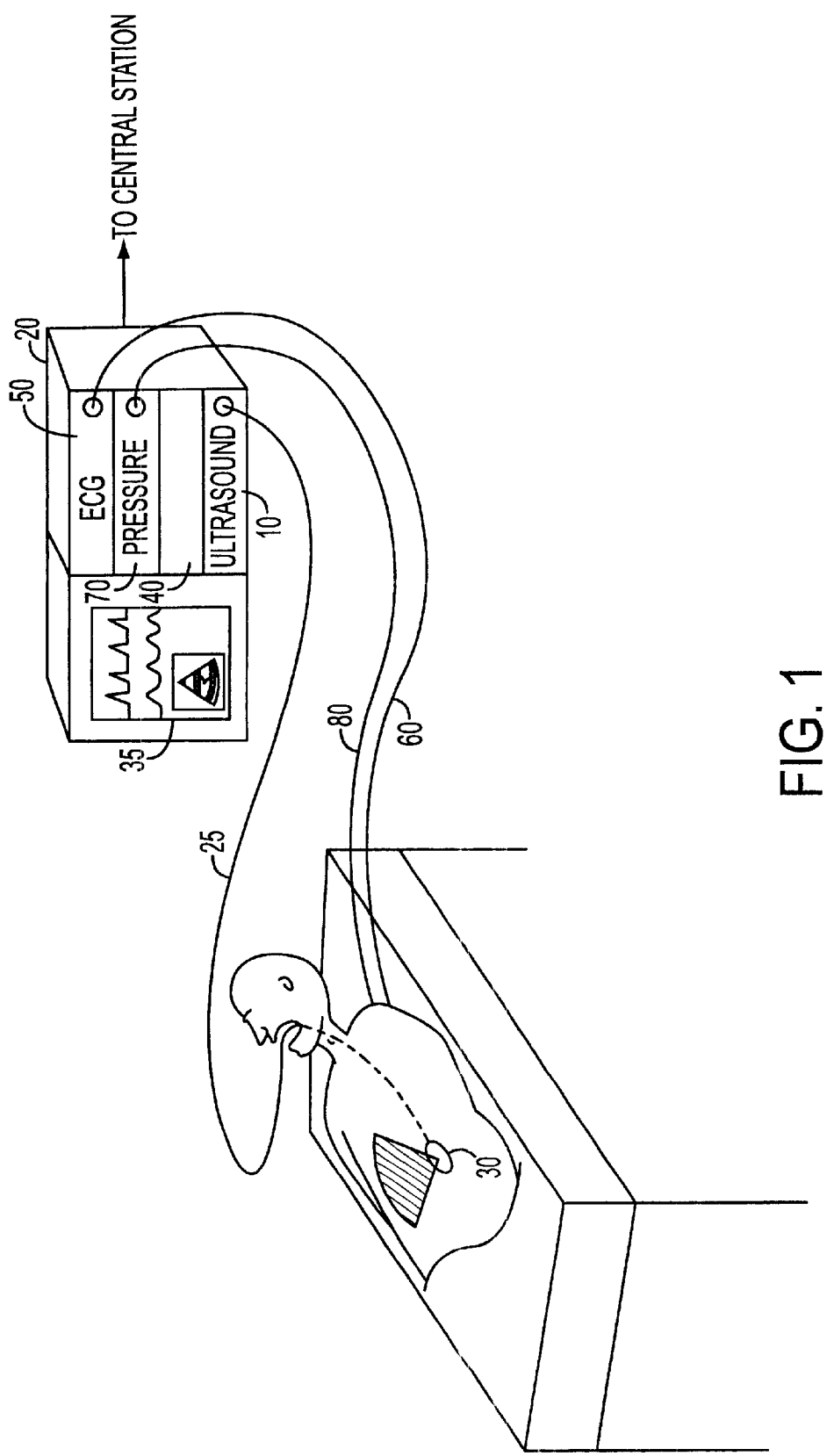
FIG. 1 is a schematic diagram of an embodiment of a system including an ultrasound imaging unit as a plug-in module in accordance with the present invention.

Reference will be now made in detail to the present exemplary embodiments of the present invention, examples of which are illustrated in the accompanying drawings, wherein like reference numerals refer to the like elements throughout.

Patient monitoring functions are routinely performed on a variety of patients in many different settings of clinical usage, for instance intensive care units, surgical recovery units, individual patient monitoring, etc. Parameters obtained from the patient monitoring functions typically include cardiac functions (i.e., EKG, blood pressure, etc.), temperature, respiration, fetal activity, etc. These parameters are taken in a continuous period of time. In contrast, an ultrasound imaging exam for diagnostic image acquisition is typically conducted at sporadic times. Nevertheless, ultrasound imaging offers a potentially valuable adjunct to the parameters measured during patient monitoring applications, which require continuous periods of monitoring. The parameters that may be extracted from an ultrasound image, such as stroke volume would be useful when monitoring the cardiac condition in the patient.

For instance, in a recovery situation if medication is provided to the patient to correct for wall motion abnormalities in the heart, it is necessary to determine if the medication was effective. Ultrasound imaging may be used to monitor whether the medication is effective in the patient. However, determining whether the medication was effective requires that the heart be monitored for a continuous period of time. Thus, an ultrasound imaging enhancement unit in accordance with the present invention, would execute an ultrasound imaging exam for a continuous period of time, necessary to monitor the effectiveness of medication.

A variety of algorithms could be applied to the ultrasound imaging unit as applied to patient monitoring applications. Such applications enable much more autonomous operation of the ultrasound imaging unit than conventional diagnostic imaging situations, which require a sonographer to be present full time with the patient.

The ultrasound imaging unit may implement a conventional automatic gain control to optimize the image gain, contrast, etc. The automatic gain control would be useful in initial setup of the ultrasound imaging unit to acquire an ultrasound image with minimal manual intervention, to maintain the image quality overtime, and to compensate for patient motion.

Conventional algorithms that may be modified and implemented into the ultrasound imaging unit to continuously extract from the ultrasound image patient monitoring parameters are, for instance, an automatic boundary extraction algorithm and regional wall motion algorithm. The automatic boundary extraction algorithm delineates boundaries of cardiac chambers, allowing derivation a several clinically useful measurements for cardiac monitoring applications. Conventional integrated backscatter methods could be employed for such boundary recognition. Further, kinesis measurements of tissue motion may be employed in the ultrasound imaging unit to continuously obtain contractility measurements, utilizing Doppler techniques, or others. As previously set forth, current ultrasound monitoring systems execute the algorithms in a non-continuous manner. The ultrasound imaging unit of the present invention modifies these algorithms by executing the algorithms in a continuous manner. Accordingly, the present invention provides for an ultrasound imaging unit allowing a physician to continuously extract from ultrasound images physiological data from a patient. This data, collected continuously over a period of hours or days, would allow generation of long-term trend analysis of physiological functions. Such trend data could be correlated against interventional measures to provide feedback information on the intervention's efficacy. Such ultrasound based feedback is very difficult to obtain from the present intermittent imaging methodologies.

In current ultrasound systems, once the user connects the ultrasound system to the patient or a TEE probe is inserted into the patient, the user places cursors or markers on the image of the heart to define what specific region of the heart the algorithm should be confined to analyze. Once the user determines the particular region of the heart that must be monitored, the user then selects a particular algorithm to be executed. During execution, the algorithm extracts required information and outputs a numeric number or a short-term waveform of the response of the heart versus time on a heartbeat by heart beat basis.

In contrast, the ultrasound imaging unit of the present invention would require less user intervention and less user sophistication. Specifically, once the user connects the ultrasound imaging unit to the patient or the TEE probe is inserted into the patient, the ultrasound imaging unit could automatically analyze and determine the region of the heart that needs to be monitored. In a display unit, the user would be able to see the window or region determined by the algorithm in the ultrasound imaging unit that requires attention. The ultrasound imaging unit may incorporate alarms indicating to the user whether the patient's cardiac functions, such as stroke volume, contractility, etc. have exceeded a predetermined threshold. Accordingly, the ultrasound imaging unit would continuously acquire patient monitoring information and present the information as trend data rather than instantaneous data.

The ultrasound imaging unit may be connected to a hospital network for remote monitoring. The ultrasound imaging unit may include a communication channel to download to the hospital network patient monitoring information. Thus, control of the ultrasound imaging unit may be autonomous, contained as "smart" control algorithms in the ultrasound imaging unit, or remotely controlled from a central station in the hospital. Further, the ultrasound imaging unit of the present invention may provide a remote override capability where if a physician at a remote location does not like the information provided from the ultrasound imaging unit, the physician may manually override and control the ultrasound imaging unit remotely. Thus, the ultrasound imaging unit of the present invention is flexible where a physician may monitor multiple patients from the central station and remotely control the patient monitoring unit to continuously optimize an ultrasound image and thereby obtain optimized physiological information from each patient.

The information downloaded via the communication network may include basic images, monitoring information derived from the images, or other ultrasound information. The ultrasound imaging unit may itself derive the monitoring information, or the ultrasound images would be directly downloaded to the central station and processed by a remote information processor at the central station to derive therefrom the monitoring information.

FIG. 1 is a schematic diagram of an embodiment of a system including an ultrasound imaging unit as a plug-in module 10, which is plugged into a bedside patient monitor unit 20. A cable 25 is connected from the ultrasound plug-in module 10 to a probe, such as a TEE probe 30 or an endoscope in the patient to monitor cardiac activity. The TEE probe 30 may be remotely manipulated or monitored from a central station via the communication channel in the ultrasound plug-in module 10 or may be manipulated from the bedside patient monitor unit 20 to obtain different views and direct the transducer in the TEE probe 30 to a particular region of the heart to obtain an optimal view of the heart. The communication channel may include a communication cable, an infrared (IR) port, a telephone modem, a wireless modem, or a business intranet connection. Thus, the output from the patient monitor unit 20 may be connected to a communication network of the central location, such as a clinical institution to allow immediate access to information derived from the ultrasound images for patient monitoring activities.

The patient monitor unit 20 is a modular device including a display 35, which the physician monitors at the bedside. Multiple small modules 40 are provided that plug into various slots within the patient monitor unit 20. For instance, if it is necessary to monitor a patient's ECG, then an ECG module 50 is plugged into the patient monitor unit 20. A cable 60 is connected from the ECG module 50 to electrodes on the patient. Similarly, if the physician is monitoring blood pressure, a blood pressure module 70 is plugged into the patient monitor unit 20 and a cable 80 is connected from the blood pressure module 70 to a pressure transducer (not shown) on the patient. In this instance, the algorithms extracting the patient information from the ultrasound images may be stored and executed by the ultrasound plug-in module 10, by the patient monitor unit 20, or by a remote processor at the remote location. The algorithms would generate the ultrasound displays and may process pressure waveforms, cardiac waveforms, and ultrasound waveforms in a continuous manner. Further, the algorithms would process the image information to provide patient monitoring information. The information received and/or processed at the patient monitor unit 20 may be downloaded to the remote processor at the central station and displayed for observation at that station.

Information gained from the ultrasound imaging unit may be used to generate trend line data for analysis by clinical staff. It could also be integrated with other clinical data obtained from other algorithms that may be implemented into the patient monitoring system. For example, combining stroke volume with pressure data could prove useful in analysis of cardiac workload capability.

An alarm may be triggered at the bedside and/or at the central station if the processor determines from the waveforms that the patient's diagnostics exceed predetermined thresholds. A physician at the central station may send a feedback signal via the network to the patient monitor unit 20 to manipulate the ultrasound image to optimize the image, to manipulate the TEE probe 30, or to command further testing.

Figure 2:
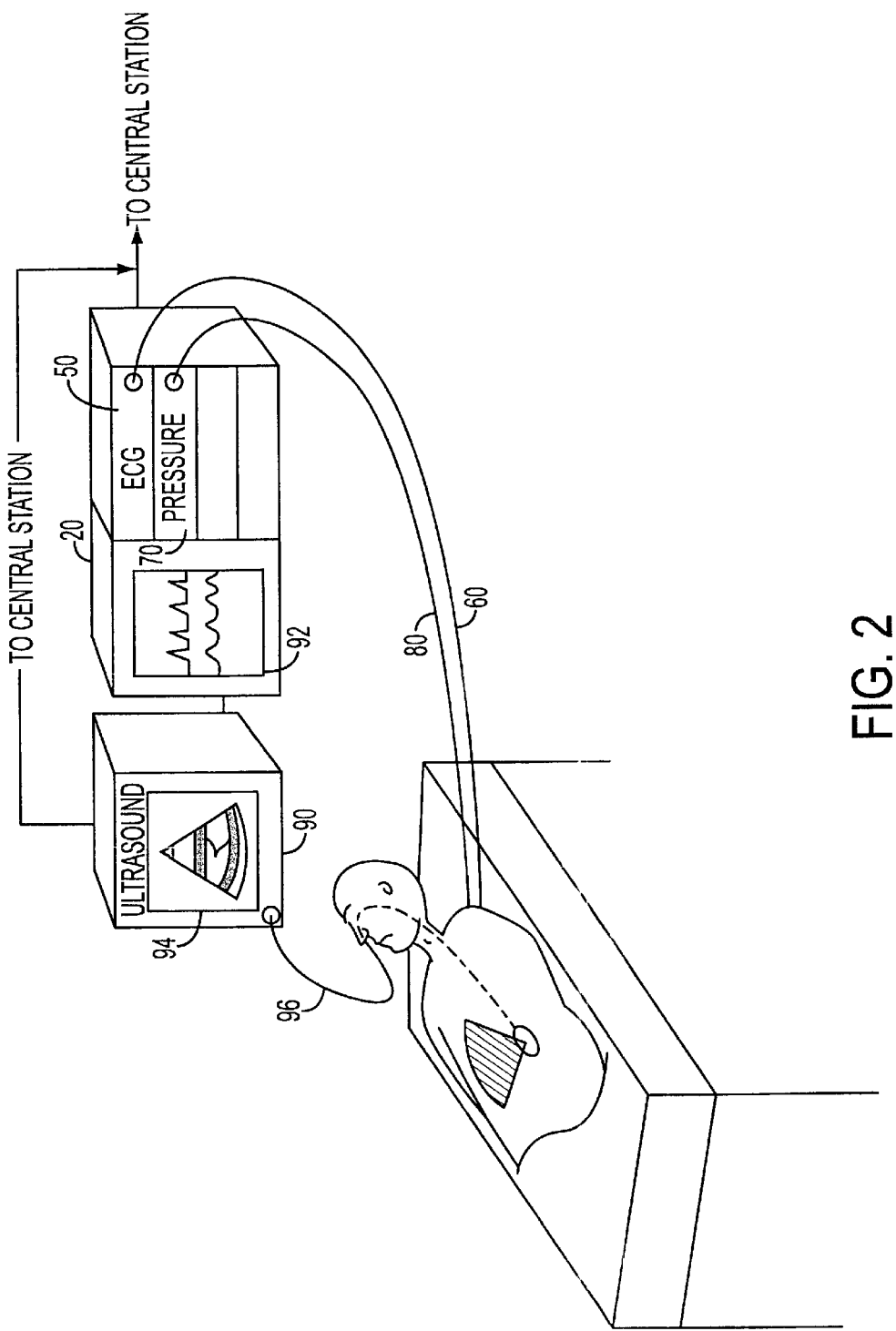
FIG. 2 is a schematic diagram of an embodiment of a standalone ultrasound imaging unit in accordance with the present invention.

FIG. 2 is a schematic diagram of an embodiment of a standalone ultrasound imaging unit 90. The standalone ultrasound imaging unit 90 is connected to the patient monitor unit 20. The control, operation, and exchange of patient information between the patient monitor unit 20, the ultrasound imaging unit 90, and the central station are described in FIG. 1.

The patient monitor unit 20 and the ultrasound imaging unit 90 each may independently or concurrently download patient monitoring information to the central station. The ultrasound imaging unit 90 may process the ultrasound images obtained to generate patient monitoring information or may download the images to the patient monitor unit 20 or the central station for processing. A cable 96 is connected from the ultrasound imaging unit 90 to a trans-nasal TEE probe, entering the patient through a nasal passage, residing in the esophagus.

FIG. 2, the ultrasound imaging unit 90 is illustrated as a dedicated display unit. A separate display unit 92 on the patient monitor unit 20 displays waveforms from the ECG module 50 and the blood pressure module 70. The patient monitor display unit 92 may be used to also display ultrasound derived images or data. The ultrasound imaging unit 90 may include sophisticated image demodulation techniques, such as acoustic quantification or color kinesis or regional wall motion, which is an algorithm to determine abnormal heart wall motions. These sophisticated image demodulation techniques could be applied to the ultrasound image information by either local processing, or remote processing capability.

Either ultrasound imaging unit shown in FIGS. 1 and 2 may be incorporated in an ambulatory vehicle, where a user would not be required to have expertise in monitoring cardiac activity, for instance. The user would download the images via an RF connection, for instance, to a hospital network where the physician would be able to read the images and to obtain therefrom continuous diagnostic data from the patient. The physician may then communicate with the user of the system recommending treatment or medication to the patient while continuously monitoring the patient's condition. In the alternative, the physician may remotely control the ultrasound imaging unit.

Figure 3A:
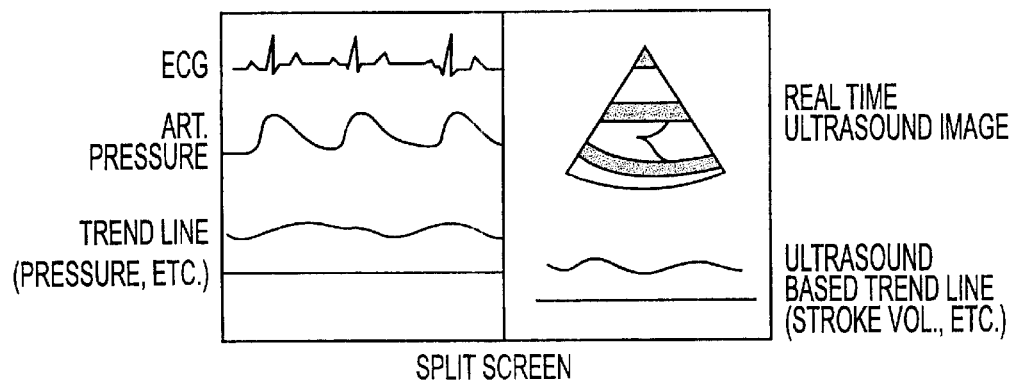
FIG. 3A is a display unit showing a split screen display.
Figure 3B:
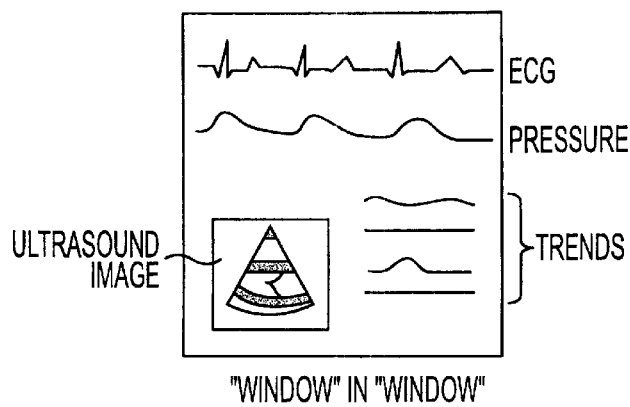
FIG. 3B is a display unit showing a "window-in-window" display.

FIG. 3A is a schematic diagram of a split screen display displaying the patient's physiological parameters including ECG and blood pressure, and related trend lines on one side of the screen. The ultrasound image and related trend lines extracted from the ultrasound image are shown on the other side of the screen. FIG. 3B is a schematic diagram of a display unit showing a "window-in-window" display. Here, the ultrasound image and related trend lines extracted from the ultrasound image are shown as a smaller window within the main patient monitoring window. ECG, blood pressure, and related trend lines are also displayed on the same display.

Figure 4:
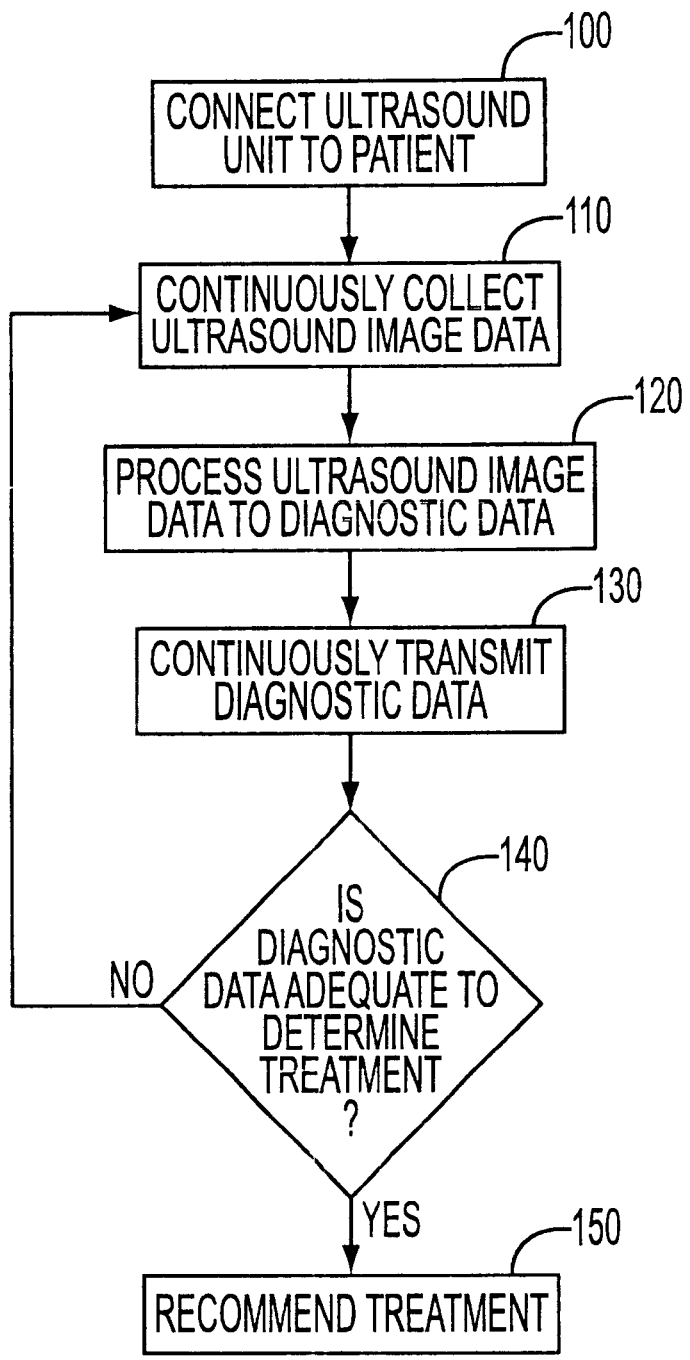
FIG. 4 is a flow chart illustrating a method embodiment of the present invention.

As illustrated in FIG. 4, a flow chart illustrating a method embodiment of the present invention is shown. At operation 100, the user of the ultrasound imaging unit 10, 90 inserts the TEE probe 30 into the patient. At operation 110, the ultrasound imaging unit 10, 90 continuously collects ultrasound image data. At operation 120, the ultrasound imaging unit 10, 90, the patient monitor unit 20, or a remote processing station, such as the central station, continuously processes the ultrasound image data collected to diagnostic data. At operation 130, the ultrasound imaging unit 10, 90 or the patient monitor unit 20 continuously transmits the diagnostic data to the physician at another location to analyze the diagnostic data. At operation 140, if the diagnostic data is adequate to determine a medical treatment for the patient, then, at operation 150, the physician recommends the medical treatment for the patient to the user. Otherwise, from operation 140, the method returns to operation 110 where the procedure is repeated to continuously obtain the diagnostic data.

Accordingly, the present system provides for an ultrasound imaging unit, integrated into a patient monitoring system to generate continuously and in real-time physiological information from an ultrasound image. Further, the ultrasound imaging unit, according to the present invention, provides flexibility to a user by allowing a physician to monitor multiple patients from a central location and remotely control the patient monitoring unit including the ultrasound imaging unit. The system would be able to automatically regulate and control the ultrasound-monitoring module to generate an optimal ultrasound image.

Although a few preferred embodiments of the present invention have been shown and described, it would be appreciated by those skilled in the art that changes may be made in this embodiment without departing from the principles and spirit of the invention, the scope of which is defined in the claims and their equivalents.

What is claimed is:

1. An apparatus, comprising:
    a patient monitoring system for generating patient monitoring information; and
    an ultrasound imaging unit integrated into the patient monitoring system, the ultrasound imaging unit configured to continuously generate ultrasound images from a patient and including algorithms configured to continuously extract therefrom, in response to the ultrasound images, physiological diagnostic data corresponding to adjunct physiological functions of the patient monitoring information and to generate ultrasound based trend analysis data of the physiological functions, wherein the algorithms include at least one of an automatic boundary extraction algorithm, regional wall motion algorithm, an automatic gain control algorithm, kinesis measurement, and a physiological measurement.

2. The apparatus as recited in claim 1, wherein the ultrasound imaging unit is integrated into the patient monitoring system as a plug-in unit.

3. The apparatus as recited in claim 1, further comprising a communication channel integrated with at least one of the patient monitoring system and the ultrasound imaging unit, wherein the ultrasound imaging unit is further configured to continuously transmit the diagnostic data using the communication channel for receipt at a remote location.

4. The apparatus as recited in claim 3, wherein at least one of the patient monitoring system and the ultrasound imaging unit are further responsive to a remote control signal received from the remote location, wherein the remote control signal remotely controls the continuous extraction of the diagnostic data from the ultrasound images.

5. The apparatus as recited in claim 1, wherein the ultrasound imaging unit is coupled to a probe insertable through a mouth or a nose of the patient to monitor a desired region of the patient for a continuous period of time.

6. The apparatus as recited in claim 5, further comprising a communication channel integrated with the ultrasound imaging unit, wherein the probe is responsive to a remote control signal, received via the communication channel in the ultrasound imaging unit, for being manipulated remotely via the communication channel in the ultrasound imaging unit.

7. The apparatus as recited in claim 1, wherein the ultrasound imaging unit is further configured to automatically analyze and determine a region of a heart of the patient to be monitored.

8. The apparatus as recited in claim 7, wherein the ultrasound imaging unit further includes a remote override capability, wherein the remote override capability is configured for allowing a person at a remote location to override and manually determine the region of the heart of the patient to be monitored.

9. The apparatus as recited in claim 1, wherein the patient monitoring system includes slots adapted to receive modules, the modules comprising at least one of a blood pressure module and an ECG module to monitor a patient's blood pressure and ECG signals, respectively.

10. The apparatus as recited in claims 9, wherein the ultrasound imaging unit includes a communication channel, the communication channel configured to download to a hospital network at least one of the ultrasound images, the diagnostic data, the blood pressure signals, and the ECG signals.

11. The apparatus as recited in claim 1, further comprising a display screen, the display screen configured for displaying the ultrasound images and the diagnostic data.

12. The apparatus as recited in claim 11, further comprising a split screen display, the split screen display configured for displaying patient monitoring data and related trend lines in a first portion of the split screen display and for displaying the ultrasound images and related trend lines extracted from the ultrasound images in a second portion of the split screen display.

13. The apparatus as recited in claim 11, further comprising a window-in-window display, the window-in-window display configured for displaying patient monitoring data and related trend lines in a first window together with the ultrasound images and related trend lines extracted from the ultrasound images in a second window, the second window being within the first window.

14. The apparatus as recited in claim 1, further comprising an alarm for indicating that a patients physiological parameter has exceeded a predetermined threshold, wherein the alarm is triggered by at least one of the ultrasound images and the diagnostic data, wherein the diagnostic data comprising at least one selected from the group consisting of stroke volume, heart rate, and blood pressure.

15. An apparatus, comprising:
a patient monitoring system for generating patient monitoring information; and
a compact standalone ultrasound imaging unit connected to the patient monitoring system, the ultrasound imaging unit configured to continuously collect ultrasound images from a patient and including algorithms configured to process the ultrasound images to continuously extract therefrom, in response to the ultrasound images, physiological diagnostic data corresponding to adjunct physiological functions of patient monitoring information and to generate ultrasound based trend analysis data of the physiological functions, wherein the algorithms include at least one of an automatic boundary extraction algorithm, a regional wall motion algorithm, an automatic gain control algorithm, a kinesis measurement, and a physiological measurement.

16. The apparatus as recited in claim 15, wherein the ultrasound imaging unit is further responsive to a remote control signal received via a communication channel from a remote location, wherein the remote control signal remotely controls the continuous extraction of the diagnostic data from the ultrasound images.

17. The apparatus as recited in claim 16, wherein the communication channel includes at least one selected from the group consisting of a communication cable, an infrared (IR) port, a telephone modem, a wireless modem, and an intranet connection.

18. The apparatus as recited in claim 15, wherein the ultrasound imaging unit is further configured to automatically analyze and determine a region of a heart of the patient to be monitored.

19. The apparatus as recited in claim 18, wherein the ultrasound imaging unit further includes a communication channel and a remote override capability, wherein the remote override capability is configured for allowing a person at a remote location to override the automatic determination via the communication channel and manually determine the region of the heart of the patient to be monitored.

20. The apparatus as recited in claim 15, wherein the ultrasound imaging unit further includes a communication channel and a probe coupled to the ultrasound imaging unit, wherein the probe is responsive to a remote control signal, received via the communication channel, for being manipulated remotely via the communication channel in the ultrasound imaging unit.

21. The apparatus as recited in claim 15, wherein the ultrasound imaging unit includes a communication channel, the communication channel configured to download to a hospital network at least one of the ultrasound images and the diagnostic data.

22. The apparatus as recited in claim 15, further comprising a display screen, the display screen configured for displaying the ultrasound images and the diagnostic data.

23. The apparatus as recited in claim 22, further comprising a split screen display, the split screen display configured for displaying patient monitoring data and related trend lines in a first portion of the split screen display and for displaying the ultrasound images and related trend lines extracted from the ultrasound images in a second portion of the split screen display.

24. The apparatus as recited in claim 22, further comprising a window-in-window display, the window-in-window display configured for displaying patient monitoring data and related trend lines in a first window together with the ultrasound images and related trend lines extracted from the ultrasound images in a second window, the second window being within the first window.

25. The apparatus as recited in claim 15, further comprising an alarm for indicating that a patient's physiological parameter has exceeded a predetermined threshold, wherein the alarm is triggered by at least one of the ultrasound images and the diagnostic data, wherein the diagnostic data comprising at least one selected from the group consisting of stroke volume, heart rate, and blood pressure.

26. A method comprising:

integrating an ultrasound imaging unit to a patient monitoring system, wherein the ultrasound imaging unit is configured to continuously generate ultrasound images from a patient and includes algorithms configured to continuously extract therefrom, in response to the ultrasound images, physiological diagnostic data corresponding to adjunct physiological functions of patient monitoring information and to generate ultrasound based trend analysis data of the physiological functions, wherein the algorithms include at least one of an automatic boundary extraction algorithm, a regional wall motion algorithm, an automatic gain control algorithm, a kinesis measurement, and a physiological measurement;

connecting the ultrasound imaging unit to a patient; and continuously collecting ultrasound imaging data from the patient with use of the ultrasound imaging unit of the patient monitoring system.

27. The method as recited in claim 26, further comprising:

continuously transmitting the diagnostic data using a communication channel to a location remote from the patient monitoring system and the ultrasound imaging unit.

28. The method as recited in claim 27, further comprising:

analyzing the physiological diagnostic data and determining therefrom a medical treatment for the patient.

29. The method as recited in claim 26, further comprising:

automatically determining and analyzing a region of a heart of the patient to be monitored using the ultrasound imaging unit.

30. The method as recited in claim 26, further comprising:

providing a remote override capability, wherein the remote override capability is configured for allowing a person to override and manually control the ultrasound imaging unit.

31. The method as recited in claim 26, further comprising:

continuously transmitting via a communication channel the ultrasound imaging data and the physiological diagnostic data.

* * * * *